United States Patent [19]
Kenney

[11] Patent Number: 5,969,227
[45] Date of Patent: Oct. 19, 1999

[54] APPARATUS AND METHOD FOR TESTING LUBRICITY

[75] Inventor: Norman P. Kenney, Houston, Tex.

[73] Assignee: Newpark Drilling Fluids, Inc., Houston, Tex.

[21] Appl. No.: 09/016,514

[22] Filed: Jan. 30, 1998

[51] Int. Cl.⁶ .................................................. G01N 19/02
[52] U.S. Cl. .............................................. 73/10; 73/53.05
[58] Field of Search ............................. 73/150.18, 53.05, 73/10, 53.06, 61.41

[56] References Cited

U.S. PATENT DOCUMENTS

| | | | |
|---|---|---|---|
| 3,913,377 | 10/1975 | Lindeman | 73/10 |
| 4,341,115 | 7/1982 | Alekhin et al. | 73/153 |
| 4,557,142 | 12/1985 | Hensley et al. | 73/153 |
| 4,630,468 | 12/1986 | Sweet | 73/59 |
| 5,052,219 | 10/1991 | Fery et al. | 73/153 |
| 5,377,525 | 1/1995 | Hutchinson et al. | 73/9 |
| 5,616,842 | 4/1997 | Armengaud et al. | 73/152.18 |
| 5,637,795 | 6/1997 | Hale et al. | 73/152.01 |

OTHER PUBLICATIONS

Drilling Through Mature Production Zones, Kenney & Kilchrist, SPE/IADC 37607, Mar. 1997.
Preliminary Report on Effectiveness of Different Lubricants on Wear and Friction Coefficients Using Shale Medium, Hale et al., SPE/ADC 29424, Mar. 1995.
Lubricity and Wear of Shale; Effects of Drilling Fluids and Mechanical Parameters, Dzialowski et al, SPE/IADC 29424, 1999.
Drilling & Completion Fluids Second Quarter 1996 Technical Forum Lubricity pp. 5–11.

Primary Examiner—Michael Brock
Attorney, Agent, or Firm—Robert C. Shaddox

[57] ABSTRACT

A method and apparatus for determining the lubricity of an oil well drilling fluid, whereby a sample in a cell holder may be subjected to a desired pressure, temperature, kinetic friction, and lubricating fluid to simulate drilling conditions in a well bore, and particularly to simulate the drilling conditions of a non-vertical well bore such as encountered in horizontal drilling which generates sliding non-rotational frictional forces.

16 Claims, 5 Drawing Sheets

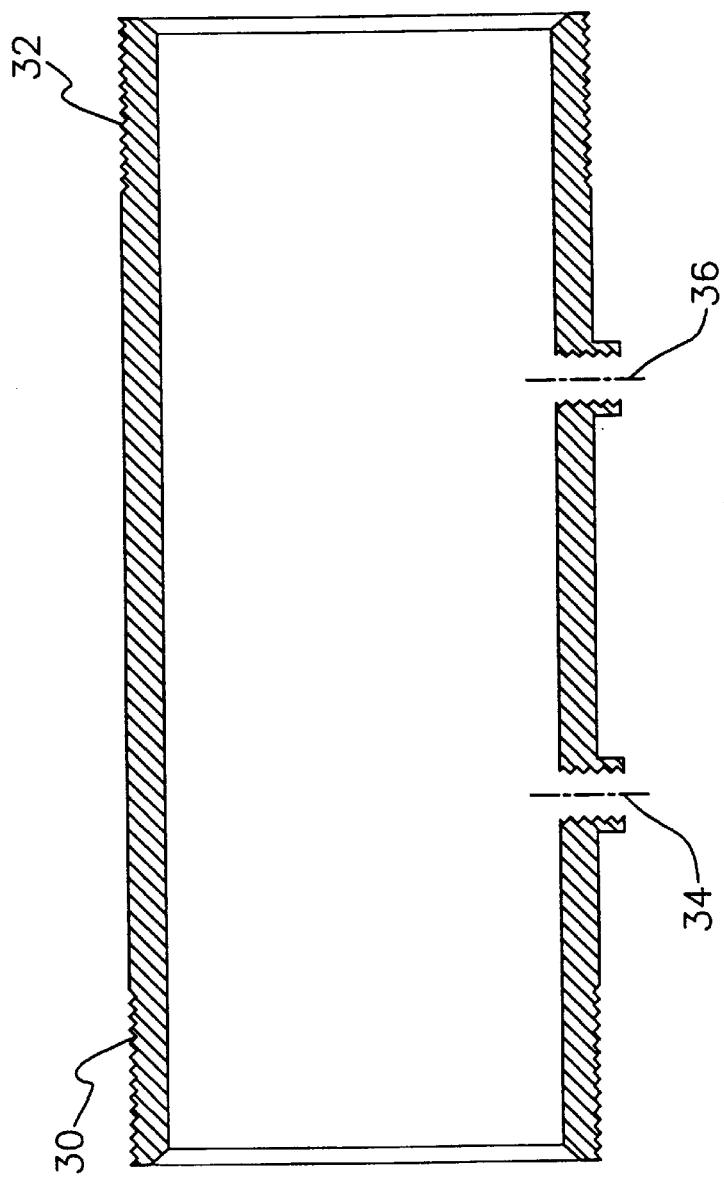
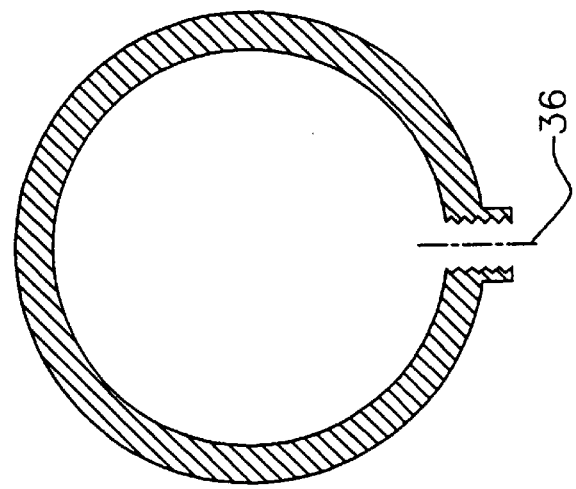

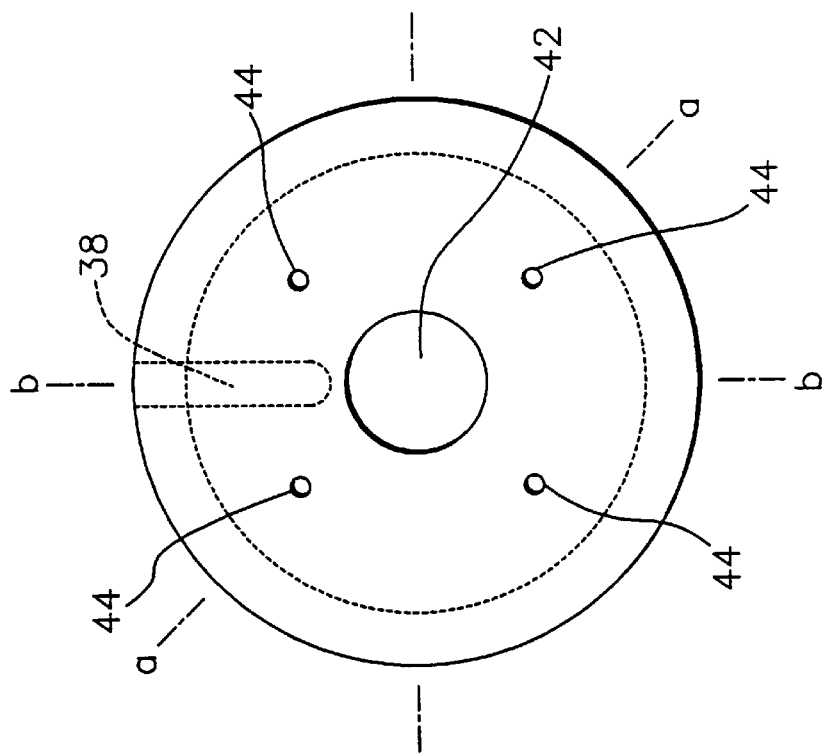
Fig. 4
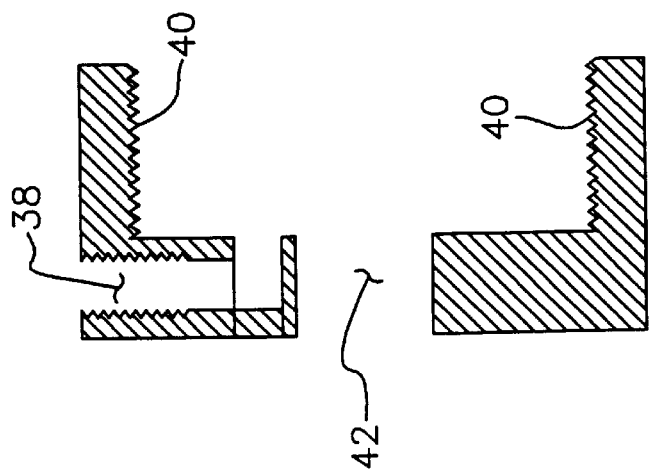
Fig. 5
Fig. 6

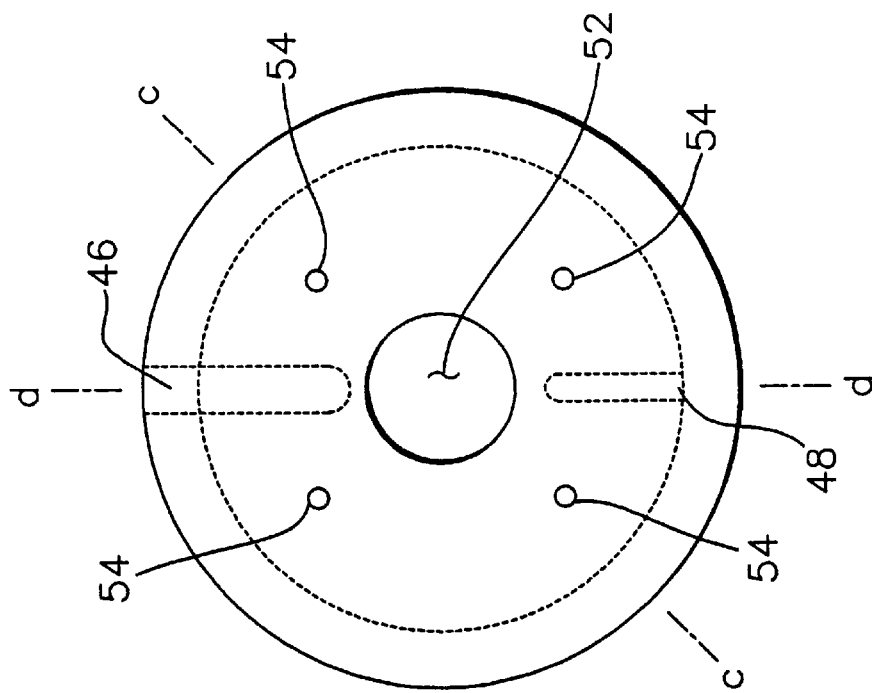
Fig. 7
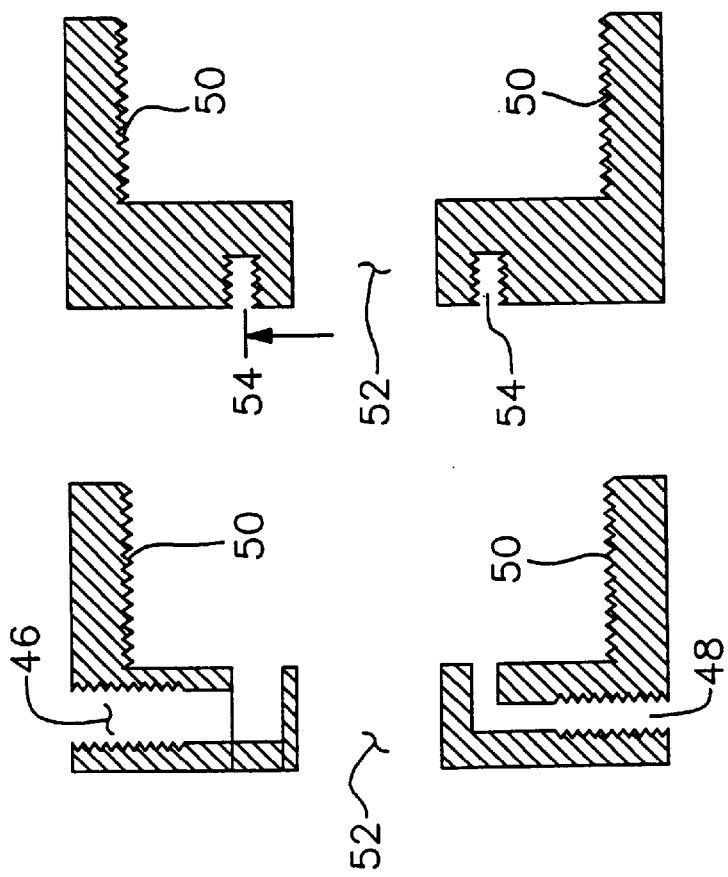
Fig. 8
Fig. 9

APPARATUS AND METHOD FOR TESTING LUBRICITY

FIELD OF INVENTION

The invention relates to an apparatus for testing the lubricity of fluids, particularly for testing drilling muds for use in drilling an oil well, and methods.

BACKGROUND OF INVENTION

Modern oil well drilling technology and techniques have opened up new oil reserves that had previously been unreachable. Technology such as improved seismic imaging identifies new reserves. Techniques such as horizontal drilling may allow these identified reserves to be reached by a well bore. Technology and know-how combine to provide a variety a non-vertical drilling approaches to reach new reserves.

These new approaches, however, have also presented new problems. One of the most significant problems is failure of the drill bit to penetrate a particular formation, resulting in stuck pipe or other drilling stoppages. Excessive friction between the well bore and the drill or pipe is the usual culprit in such drilling failures.

Drilling and completion engineers continually face the problem of overcoming resistances to drilling the wellbore or placing production equipment into a newly completed well. Most frictional forces encountered in drilling are due to hole conditions and geometry.

No hole is truly vertical. Drill pipe, casing, screens, and the like, will come in contact with the wellbore at numerous points. The problem is exacerbated in deviated wellbores. Modern wellbores may be slanted, horizontal, or may even turn back toward the surface. Frictional resistance is commonly referred to as drag in the context of a non-vertical wellbore.

Drill lubricating fluids, also known as muds, are commonly supplied to a drill to reduce the coefficient of friction where the drill, pipe, or equipment contacts the formation being drilled. By way of example and not limitation, muds include chemicals, fluids, and fluid systems such as oil mud, parafin oil, olefin oil solutions, water-based mud, synthetic systems, blendes, calcium chloride brine, emulsified or ground gilsonite, straight chain normal hydrocarbons. A mud may also comprise a collection of products.

The lubricity of a mud is important for enhancing the economics of drilling and completing high angle holes. Lubricity is a measure of the coefficient of friction between a moving part and a surface in contact with the part. The lower the coefficient of friction, the greater the lubricity. The coefficient of friction, u, is defined as the ratio of the force, F, required to move an object in contact with a surface to the force, $W_1$, pushing downward or perpendicular to the object: $u=F/W_1$. The coefficient of friction may alternatively be called the friction coefficient, friction factor, or the lubricity coefficient.

The lubricity of a mud is a measure of the mud's ability to lower torque and drag forces. Muds are frequently tested in the laboratory to obtain a rough estimate of the mud's lubricity before the mud is used in the field. It is important for the economics of drilling, and to keep the drilling operation out of trouble, that the laboratory measurements of lubricity reliably correlate to the lubricity observed in the field. Drill operators depend on reliable lubricity coefficients as input into computer drilling models that predict drillstring loads to optimize casing runs. The friction coefficient is used in these models prior to drilling the well to enhance the well design with respect to torque and drag. Drilling fluid (mud) companies depend on reliable friction coefficients to recommend proper mud systems, determine the optimum lubricant amounts, and to develop new lubricant additives.

A variety of lubricity measuring machines have been developed by the oil industry. The earliest machines were adapted from other industries.

To evaluate lubricants for torque reduction, an early device, the Timken lubricity tester, was adapted from an industry standard extreme pressure (EP) torque measuring instrument. This early apparatus was used to determine the friction coefficient under high loads and extremes pressures, such as observed in bearings and engines.

The first mud lubricity tester was modified from the Timken apparatus, and was used to identify extreme pressure lubricants to extend the life of bit bearings. The advent of sealed bearing bits has rendered these lubricants obsolete.

The Fann instrument was developed to test lubricity under substantially vertical conditions. It uses a steel block to simulate the wall of a hole. The block is pressed against a rotating steel ring by a torque measuring arm. The coefficient of friction is determined by the amount of current required to drive the rotating ring at a given rpm while the steel block is immersed in the mud. The current drawn by the device is converted to a lubricity coefficient by a previously calibrated chart. The Fann device tests lubricants under standard conditions to see how they compare under those conditions.

Another lubricity tester is the Lubricity Evaluation Monitor (LEM). The LEM differs from the Fann machine in that the mud is continuously circulated across the test surfaces, and it can use a sandstone core, shale pieces, filter cakes or steel pipe as a test medium. A stainless steel shaft rotates under an applied load. The load forces the shaft into the test medium, and the torque required to turn the shaft is plotted against time. The LEM tests lubricants under a variety of conditions.

Yet another lubricity tester is the HPHT lubricity tester (HLT). The HLT was developed to address problems with previous testers. One problem with the Fann and LEM machines is that the coefficients derived are not scalable to actual downhole conditions. This is particularly true with respect to temperatures and pressures encountered downhole. The HLT was developed in an effort to more accurately simulate downhole conditions.

The primary components of the HLT consist of a friction mechanism contained in a test cell, a lathe frame onto which the test cell is mounted, mud circulation and fluid injection means (separately housed), and a computerized control, monitoring and display system.

HLT, like the Fann and LEM devices, is best suited for simulating substantially vertical drilling conditions. Furthermore, these devices essential model static drilling conditions which may not accurately simulate the dynamic nature of actually drilling.

Non-vertical, deviated, and dynamic conditions, however, present a different set of torque and resistance problems than those modeled by the prior art. For example, drag, the resistance to drilling encountered by deviated drilling conditions, is not well modeled by the above devices.

A particular problem in modeling a horizontal drilling operation is that typical models for conventional (vertical) drilling use rotation to generate data, but horizontal drilling operations more often use a mud motor and do not rotate the drill string. Horizontal sliding forces are not the focus of prior art devices.

Lubricants that are successful under vertical conditions may not be successful under deviated conditions.

To effectively test lubricants under dynamic field circumstances, a portable lubricity evaluation device that could be transported to the drill site for testing muds under the precise conditions being encountered in the field would provide great benefits for drilling success, economies, and efficiency.

Absent an on-site lubricity testing apparatus, core samples, filter cake, and other indicia of drilling conditions, must be sent to the nearest laboratory to develop an optimal fluid in response to the indicia. The mud, or instructions for its formulation, must then be sent to the field for implementation.

Remote mud analysis means delays of hours or days in drilling, and is subject to miscommunication or delayed communication about the drilling operation. A portable lubricity evaluation device that could be brought to the drilling site would obviate these problems.

The value of identifying the optimal drilling mud is presented in the following example.

A drilling program in south Texas was initiated on the basis of 3-dimensional seismic data that revealed untested deep zones in six wells beneath the depth of 12500 feet where production had stopped. Among the objectives of the program was to reach the untested reserves below 12500 feet and to optimize drilling efficiency. During the course of the program, the selection of drilling fluids became the central issue in optimizing drilling efficiency.

At the beginning of the project, it was not anticipated that stuck pipe would be a major problem, because the field, which had produced for twenty years, did not have a history of stuck pipe. The first three wells that were drilled, however, all failed as a result of stuck pipe. The abundance of stuck pipe problems revealed that there were multiple pressure depleted zones at the depth of interest. As a result of the failure of the first three wells, the selection of drilling fluid came under increased scrutiny.

The choice of drilling fluids was amended for the remaining three wells of the program. Oil based muds were eliminated from consideration, and an economical water based mud was specified. Additives that were readily available in the field were used. Ultimately, a bentonite based drilling fluid with an EP lubricant, gilsonite, and micronized cellulose fiber additive was selected.

The results in the last three wells were dramatically different from the experience of the first three wells. Each of the last three wells was a success. The mud was modified as needed based on the condition of the filter cake and drilling conditions.

The program described above took advantage of a portable dynamic filtration apparatus to evaluate the filter cake of the drill operation on-site. Muds were designed on the basis of filter cake results. The program did not, however, have use of a portable lubricity evaluation device of the present invention. The example is provided to illustrate the impact that the drilling fluid can have on the success of a well. It will be understood by those skilled in the art that access to a lubricity testing apparatus on-site would have enhanced the efficiency of the program described above.

Therefore, it is an object of the present invention to provide a lubricity evaluation device that simulates non-vertical drilling conditions to measure the effectiveness of a lubricant against drag and other frictional resistance forces encountered in non-vertical or deviated holes. The disclosed embodiment permits measurement of data that enables the calculation of a coefficient of friction for sliding without rotation.

It is also an object of the present invention to provide a lubricity evaluation device that can measure the lubricity of a fluid under a variety of load, torque, pressure, temperature, and frictional conditions.

It is a further object of the present invention to provide a lubricity evaluation device that can test a fluid under dynamic conditions encountered in the field.

It is another object of the invention to provide a portable lubricity evaluation device.

SUMMARY

These and other objects of the invention are achieved in a horizontal friction lubricity evaluation device of one embodiment of the present invention. An apparatus of the primary embodiment comprises four basic components:

1. Main body. The main body comprises the test cell, the linear actuator, and the rotation motor.
2. Instrument Control Unit. The instrument control unit controls the linear actuator rotational motor, temperature, and the pneumatic cylinders. It regulates the temperature of the mud reservoir as well as cell heating elements. The instrument control unit may also control $N_2$ pressure supplied to the cell.
3. Mud handler. The mud handler comprises the MUD pump and the heated MUD reservoir. These components control the flow of mud, including velocity, pressure and temperature of the mud. The pump, in the primary embodiment, is a positive displacement progressive cavity pump capable of handling abrasive, neutral, or aggressive liquids with high particle content. In other embodiments a positive displacement peristaltic pump may be used. The heated mud reservoir, in one embodiment, is capable of generating mud temperatures of about 400°. The temperature of the mud, however, should never exceed the maximum operating temperature of the pump.
4. Computer. The computer is used for data collection, report writing, and calculation. In one embodiment, the computer has 166 MHZ pentium(r) microprocessors, 14 MB of RAM, 1.6 GB hard drive, and an 8X CD-ROM.

The main body comprises a test cell. The test cell should be fabricated of a suitably durable material such as stainless steel. Inside the test cell is a cell holder. The cell holder positions and holds the core sample in place during operation of the apparatus. Attached to the test cell are two pneumatic cylinders and a sealed guide pin. The cylinders apply pressure to the cell holder to simulate pressures such as drag and friction encountered in a well bore. The cylinders are pressure actuated and any suitable pressure source, such as pneumatic or hydraulic, may be used to actuate the cylinders.

The test cell is closed by end caps on each end. The end caps may be threaded to engage threads on each end of the test cell. Each end cap also has an O-ring seal holder through which the hardened steel rod passes. Incorporated into each end cap are inlet and outlet connections for the drilling fluid and a temperature probe port.

The linear actuator translates the rod through the load cell. The actuator overcomes the friction force generated by contact between the hardened steel rod and the core sample.

This force is read by the load cell that is attached to the end of the actuator screw. When activated, the actuator forces or drives the rotation motor and the rod assembly inward and outward. The rotational motor breaks the kinetic friction by rotating the rod at the start of the test.

The linear actuator provides translational kinetic friction to the core sample in the cell holder, while the motor provides rotational kinetic friction to the sample and the cylinders apply lateral pressure to simulate drag in non-vertical well bore. The combination of separately controllable translational, rotational, and lateral actions effectively simulates the wide variety of conditions in a non-vertical well bore to allow accurate determination of the lubricity of the test fluid.

The well bore core sample may be taken directly from a well in the field. Different fluids can be tested to determine the most effective lubricant for the precise geological conditions of that well bore.

The end caps ports permit the temperature, pressure and fluid conditions in the cell to be separately varied to suit any desired test conditions. The ability to vary these conditions, together with the independently regulated actions of the rotational motor, the linear actuator and the pressure actuated cylinders, allows a fluid to be tested under conditions that simulate virtually any real-world circumstance encountered in the field.

The apparatus of one embodiment of the invention is mounted on a base and is portable. The apparatus can be taken to a site in the field for testing drilling fluids on-site against the exact core samples the drill is boring through.

The portability of one embodiment of the invention provides convenience, saves time and money, and improves the efficiency of drilling operations. The embodiments disclosed would assist in drilling through geological structures that would otherwise cause drill failure by making possible the on-site identification of an effective drilling fluid to cut through the problematic formation.

The embodiments disclosed comprise an apparatus for determining the lubricity of an oil well drilling fluid. In a primary embodiment the apparatus comprises:

a base;

a cell body having two ends;

a cell holder disposed within the cell body to hold a core sample for testing;

a first end cap on one end of the cell body, the end cap comprising an O-ring seal holder to admit a rod into the cell body;

a second end cap on the other end of the cell body, the second end cap comprising a plurality of ports for inlet and outlet of fluids and samples and temperature monitoring and regulation, and further comprising an O-ring seal holder to admit a rod into the cell body;

at least one pressure actuated cylinder in contact with the cell holder to maintain the cell holder in a desired position in the cell body;

a rod axially disposed through the assembly of the cell body, cell holder, and the end caps;

a motor attached to the rod to turn the rod;

a linear actuator attached to the base and to the assembly of the cell body, cell holder, end caps, and cylinder to axially translate the assembly so that the rod axially translates in the cell holder;

whereby a sample in the cell holder may be subjected to a desired pressure, temperature, kinetic friction, and lubricating fluid to simulate drilling conditions in a well bore, and particularly to simulate the drilling conditions of a non-vertical well bore, to determine the lubricating effectiveness of the fluid.

In one embodiment, the apparatus may also comprise a guide pin attached to the cell holder to position the core sample in the cell holder;

The primary embodiment also comprises a method for determining the lubricity of an oil well drilling fluid, the method comprising:

providing an apparatus comprising a base; a cell body having two ends; a cell holder disposed within the cell body to hold a core sample for testing; a first end cap on one end of the cell body, the end cap comprising an O-ring seal holder to admit a rod into the cell body; a second end cap on the other end of the cell body, the second end cap comprising a plurality of ports for inlet and outlet of fluids and samples and temperature monitoring and regulation, and further comprising an O-ring seal holder to admit a rod into the cell body; at least one pressure actuated cylinder in contact with the cell holder to maintain the cell holder in a desired position in the cell body; a rod axially disposed through the assembly of the cell body, cell holder, and the end caps; a motor attached to the rod to turn the rod; a linear actuator attached to the base and to the assembly of the cell body, cell holder, end caps, and cylinder to axially translate the assembly so that the rod axially translates in the cell holder; whereby a sample in the cell holder may be subjected to a desired pressure, temperature, kinetic friction, and lubricating fluid to simulate drilling conditions in a well bore, and particularly to simulate the drilling conditions of a non-vertical well bore, to determine the lubricating effectiveness of the fluid;

providing a well bore core sample into the cell holder in the cell;

closing and sealing the cell with the end caps;

inserting the rod through the end caps and the cell;

providing a fluid the lubricity of which is desired to be determined in to the cell through a port in one of the end caps;

actuating the cylinders against the cell holder to provide a desired pressure to the core sample;

actuating the linear actuator to provide translational kinetic friction from the rod to the core sample in the cell holder;

activating the motor to provide rotational kinetic friction from the rod to the core sample in the cell holder; and determining the lubricity of the fluid in the cell.

The method, in further embodiments, may also comprise a guide pin attached to the cell body to position the core sample in the cell holder.

A computer may be connected to the apparatus to record data, write reports, calculate the lubricity of the test fluid, calculate the coefficient of friction, and to perform other analytical and control functions of the invention.

It is also possible to calibrate the lubricity evaluation device by first breaking the static frictional forces before taking data to calculate the coefficients of friction. This may be done by varying the period of time after the test cycle is started before the capture data is started. The test may be operated a few times to determine the length of delay that is optimal for the given combination in the test. The delay time in the primary embodiment may be controlled by computer software.

The described embodiments address a significant problem in modeling horizontal drilling operations that is not addressed by prior art devices, which do not model the sliding, non-rotational forces encountered in horizontal drilling. Conventional (vertical) drilling is typically performed by rotating the drill string. Horizontal, deviated and other non-vertical drilling operations, however, do not rotate the drill string. Horizontal drilling is typically performed with the use a mud motor, in which drilling mud drives a drilling tool at the end of the drill string, but the string itself does not rotate. Since the drill string is not rotating in horizontal drilling, there are frictional resistances, such as drag of the string along the sides of the wellbore, which are different or not encountered in vertical drilling.

Because of the differences in vertical and non-vertical drilling, muds developed by prior art lubricity testers often are not effective in a horizontal drilling operation. Horizontal sliding forces are not the focus of prior art devices. In the embodiments described herein of the present invention, the cylinders which apply pressure to the cell holder effectively model sliding, drag, and other forces acting on a drill string in a horizontal drilling operation.

BRIEF DESCRIPTION OF THE DRAWINGS

The primary embodiment of the invention may be best understood by reference to this specification and to the appended drawings.

FIG. 2 is a cross section side view of a cell body.

FIG. 3 is a cross section front view of a cell body.

FIG. 4 is a cross section top view of an end cap.

FIG. 5 is a cross section side view of the end cap of FIG. 4 along line a—a.

FIG. 6 is a cross section side view of the end cap of FIG. 4 along line b—b.

FIG. 7 is a cross section top view of another end cap.

FIG. 8 is a cross section side view of the end cap of FIG. 7 along line c—c.

FIG. 9 is a cross section side view of the end cap of FIG. 4 along line d—d.

DETAILED DESCRIPTION OF THE PREFERRED EMBODIMENT

Figure 1:
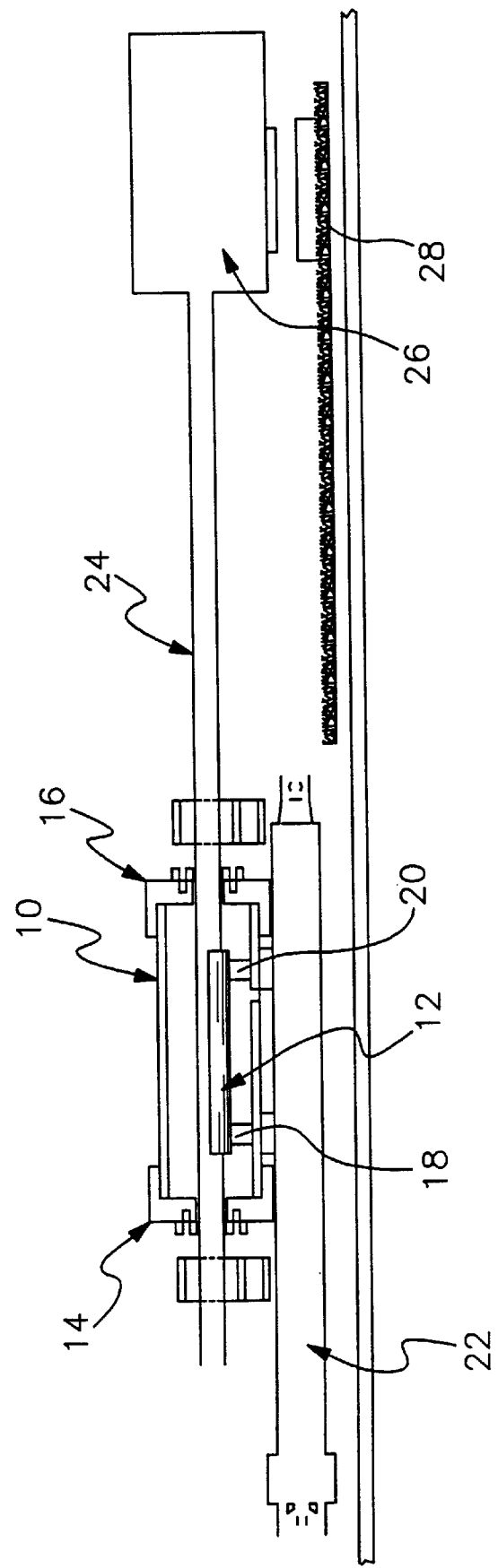
FIG. 1 is a overview of the main assemblies of the apparatus.

FIG. 1 is an overview of an apparatus of one embodiment of the present invention. The apparatus can be described in terms of two assemblies.

Assembly 1 comprises cell 10, cell holder 12 disposed within cell 10, end caps 14, 16 attached to cell 10, and pressure actuated cylinders 18, 20 in contact with cell holder 12 through cell 10. Cylinders 18, 20 apply lateral pressure to cell holder 12 to simulate drag friction encountered in a non-vertical wellbore. Cell 10 is anchored to base 28.

Assembly 2 comprises rod 24, disposed through end caps 14, 16 and cell 10 of assembly 1, and motor 26 attached to rod 24 to turn rod 24. Motor 26 is slidably attached to base 28. Linear actuator 22 is attached to assembly 2 to translate assembly 2. Linear actuator 22 translates assembly 2 relative to anchored cell 10. The effect is that rod 24 translates in cell 10 while simultaneously turning in cell 10.

FIG. 2 is a cross section side view of the cell body of FIG. 1. Ends 30, 32 are threaded to receive threaded end caps 14, 16 to close cell 10. Openings 34, 36 admit cylinders 18, 20 to apply pressure to cell holder 12. Cell 10 is made of a suitable durable material such as stainless steel.

FIG. 3 is a cross section front view of the cell body of FIG. 2. Opening 36 is shown.

FIG. 4 is a cross-section top view of end cap 14 of FIG. 1. Opening 42 admits rod 24 into cell 10 through end cap 14. O-ring seal holders 44 hold an O-ring to seal opening 42 when rod 24 is in position through opening 42. Opening 38 provides means for inlet and outlet of circulating fluid in cell 10.

FIG. 5 is a cross section side view of the end cap of FIG. 4 along line a—a. Threads 40 provide means for attaching cap 14 to cell 10.

FIG. 6 is a cross section side view of the end cap of FIG. 4 along line b—b. Opening 38 is threaded to receive a desired attachment such as a conduit to supply fluid into cell 10.

FIG. 7 is a cross-section top view of end cap 16 of FIG. 1. Openings 46, 48 provide means for inlet and outlet of fluid circulating in cell 10. Openings 46, 48 also provide means for introducing probes, such as temperature probes, or other instruments into cell 10. Threads 50 provide means for attaching cap 16 to cell 10. Opening 52 admits rod 24 into cell 10 through end cap 16. O-ring seal holders 54 hold an O-ring to seal opening 52 when rod 24 is in position through opening 52.

FIG. 8 is a cross section side view of the end cap of FIG. 7 along line c—c. O-ring seal holders 54 are threaded to receive threaded screws to secure an O-ring seal.

FIG. 9 is a cross section side view of the end cap of FIG. 7 along line d—d. Openings 46, 48 form a passageway into and out of end cap 16.

Figure 10:
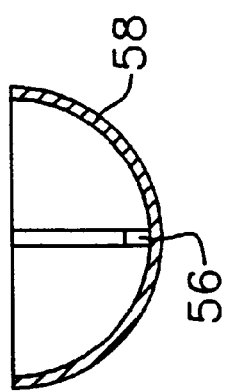
FIG. 10 is a cross section side view of a cell holder.

FIG. 10 is cross section front view of cell holder 12 of FIG. 1. Cell holder 12 comprises a modified half pipe which cradles a sample in cell 10. Ridge 56 extends axially along the interior length of cell holder 12 to secure a sample in position and to provide resistance against the sample when the apparatus is in operation. Outer surface 58 of cell holder 12 is oriented in cell 10 such that cylinders 18, 20 through openings 34, 36 of cell 10 make contact with and apply pressure to surface 58 of cell holder 12.

Figure 11:
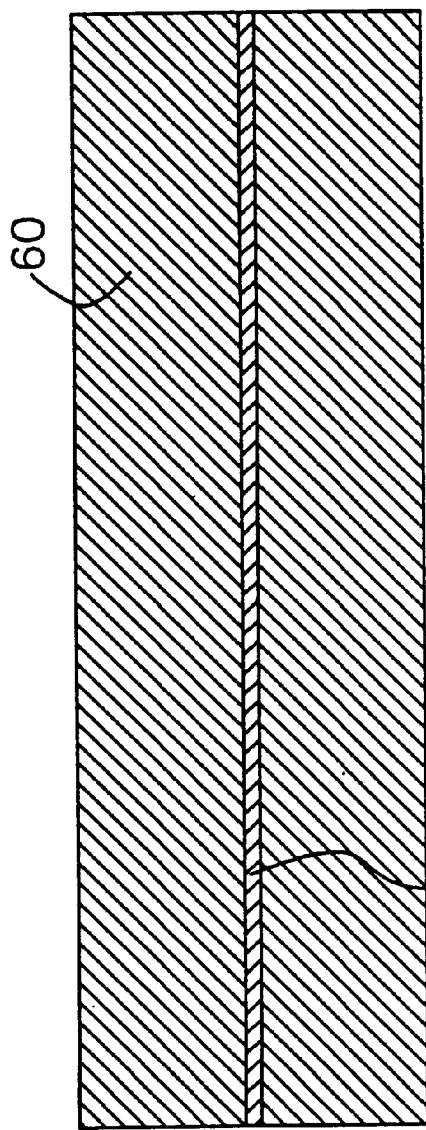
FIG. 11 is a top view of a cell holder.

FIG. 11 is a top view of the cell holder of FIG. 10. Ridge 56 extends along the center length of interior surface 60 of cell holder 10.

Figure 12:
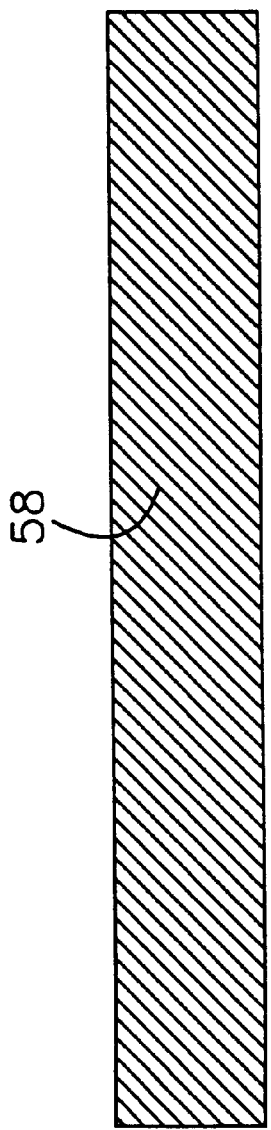
FIG. 12 is a side view of a cell holder.

FIG. 12 is a side view of the cell holder of FIG. 10. Cell 10 cooperatively receives exterior surface 58 of cell holder 12.

To perform a run of the primary embodiment, Cell holder 12 is aligned in cell 10. A core sample is aligned and placed in cell holder 12. Guide pins secure cell holder 12 in position in cell 10. End caps 14, 16 are secured to their respective ends, 30, 32. Mud inlet and outlet hoses, a temperature probe, or other desired attachments, are connected to end cap openings 38, 46, 48, as appropriate. In the primary embodiment the whole cell may bathed in fluid, and no seals are utilized to eliminate interference with the load supplied on the sample and rod. In alternative embodiments seals, of TEFLON, in the embodiment envisioned, are secured around end caps 14, 16 to prevent leakage from openings 38, 46, 48. The alternative embodiment permits supplying fluid directly to the rod/sample contact area.

Rod 24 is aligned and loaded into cell 10 through opening 52. It is recommended to inspect the O-ring attached around openings 52, 42 to confirm an adequate seal around rod 24.

The o-ring may be attached with Allen screws in threaded openings 44, 54.

A desired mud formulation is heated to a desired temperature in the mud reservoir. The pump is primed and checked for leaks. A desired pressure and mud flow rate is set. In one embodiment, heating elements in cell 10 are set to a desired temperature, typically to match the temperature of the mud, if possible.

Pressure actuated cylinders 18, 20 are actuated to press against cell holder 12 through openings 34, 36 in cell 10 at a desired pressure.

linear actuator 22 is set in the backmost position relative to slidably mounted motor 26. Mud flow is initiated into cell 10, and rotational motor 26 and linear actuator 22 are activated. linear actuator 22 moves rod 24 into cell 10, while the motor 26 rotates rod 24.

Data from the run is recorded and the lubricity and other characteristics of the mud are calculated. In one embodiment, data collection, calculation, and report writing are performed by computer.

The described embodiments solve a problem in the prior art for modeling horizontal drilling operations. Horizontal sliding forces are not the focus of prior art devices. Muds developed by prior art lubricity testers often are not effective in a horizontal drilling operation. In the embodiments of the present invention described herein, cylinders 18, 20 apply pressure to cell holder 12 to effectively model sliding, drag, and other forces acting on a drill string in a horizontal drilling operation.

The invention is described to disclose the best mode and preferred embodiment of the invention. Those skilled in the art will recognize that many modifications can be made in the described embodiment without departing from the intent and scope of the appended claims.

What is claimed is:

1. An apparatus for determining the lubricity of an oil well drilling fluid, the apparatus comprising:
    a base;
    a cell body having two ends;
    a cell holder disposed within the cell body to hold a core sample for testing;
    a first end cap on one end of the cell body, the end cap comprising an O-ring seal holder to admit a rod into the cell body;
    a second end cap on the other end of the cell body, the second end cap comprising a plurality of ports for inlet and outlet of fluids and samples and temperature monitoring and regulation, and further comprising an O-ring seal holder to admit a rod into the cell body;
    at least one pressure actuated cylinder in contact with the cell holder to maintain the cell holder in a desired position in the cell body;
    a rod axially disposed through the assembly of the cell body, cell holder, and the end caps;
    a motor attached to the rod to turn the rod;
    a linear actuator attached to the base and to the assembly of the cell body, cell holder, end caps, and cylinder to axially translate the assembly so that the rod axially translates in the cell holder;
    whereby a sample in the cell holder may be subjected to a desired pressure, temperature, kinetic friction, and lubricating fluid to simulate drilling conditions in a well bore, and particularly to simulate the drilling conditions of a non-vertical well bore, to determine the lubricating effectiveness of the fluid.

2. The apparatus of claim 1, further comprising an instrument control unit attached to the cell body to control linear actuator, the rotational motor, the temperature, and the cylinder.

3. The apparatus of claim 1, further comprising a mud handler attached to the cell body.

4. The apparatus of claim 3, wherein the mud handler comprises a progressive cavity mud pump and a heated mud reservoir.

5. The apparatus of claim 1, further comprising a computer connected to the apparatus for data collection, control functions, lubricity calculation, and report writing.

6. The apparatus of claim 1, wherein the at least one pressure actuated cylinder comprises two pressure actuated cylinders.

7. The apparatus of claim 1, wherein the at least one pressure actuated cylinder is actuated by pneumatic pressure.

8. The apparatus of claim 1, further comprising a guide pin attached to the cell to position the core sample in the cell holder.

9. The apparatus of claim 1, further comprising a seal on the first end cap and a seal on the second end cap to prevent leakage.

10. The seals of claim 9, wherein the seal comprise TEFLON.

11. A method for determining the lubricity of an oil well drilling fluid, the method comprising:
    providing an apparatus comprising a base; a cell body having two ends; a cell holder disposed within the cell body to hold a core sample for testing; a first end cap on one end of the cell body, the end cap comprising an O-ring seal holder to admit a rod into the cell body; a second end cap on the other end of the cell body, the second end cap comprising a plurality of ports for inlet and outlet of fluids and samples and temperature monitoring and regulation, and further comprising an O-ring seal holder to admit a rod into the cell body; at least one pressure actuated cylinder in contact with the cell holder to maintain the cell holder in a desired position in the cell body; a rod axially disposed through the assembly of the cell body, cell holder, and the end caps; a motor attached to the rod to turn the rod; a linear actuator attached to the base and to the assembly of the cell body, cell holder, end caps, and cylinder to axially translate the assembly so that the rod axially translates in the cell holder; whereby a sample in the cell holder may be subjected to a desired pressure, temperature, kinetic friction, and lubricating fluid to simulate drilling conditions in a well bore, and particularly to simulate the drilling conditions of a non-vertical well bore, to determine the lubricating effectiveness of the fluid;
    providing a well bore core sample into the cell holder in the cell;
    closing and sealing the cell with the end caps;
    inserting the rod through the end caps and the cell;
    providing a fluid the lubricity of which is desired to be determined in to the cell through a port in one of the end caps;
    actuating the cylinder against the cell holder to provide a desired pressure to the core sample;
    actuating the linear actuator to provide translational kinetic friction from the rod to the core sample in the cell holder;

activating the motor to provide rotational kinetic friction from the rod to the core sample in the cell holder; and determining the lubricity of the fluid in the cell.

12. The method of claim 11, wherein the apparatus further comprises a guide pin attached to the cell holder to position the core sample in the cell holder.

13. The method of claim 11, wherein the method further comprises monitoring temperature and pressure with an instrument control unit attached to the cell body to control the linear actuator, the rotational motor, the temperature, and the cylinders.

14. The method of claim 11, further comprising controlling fluid flow with a mud handler attached to the cell body.

15. The method of claim 14, further comprising controlling pressure and wherein the mud handler comprises a progressive cavity mud pump and a heated mud reservoir.

16. The method of claim 11, wherein the apparatus further comprises a computer connected to the apparatus, and wherein method comprises calculating the lubricity of the fluid with the computer.

* * * * *